(12) United States Patent
Jo et al.

(10) Patent No.: US 10,363,001 B2
(45) Date of Patent: Jul. 30, 2019

(54) MAGNETIC RESONANCE IMAGING APPARATUS

(71) Applicant: SAMSUNG ELECTRONICS CO., LTD., Suwon-si (KR)

(72) Inventors: Hyun Hee Jo, Osan-si (KR); Young Ha Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 808 days.

(21) Appl. No.: 14/684,940

(22) Filed: Apr. 13, 2015

(65) Prior Publication Data

US 2016/0015330 A1    Jan. 21, 2016

(30) Foreign Application Priority Data

Jul. 18, 2014  (KR) .................. 10-2014-0090804

(51) Int. Cl.
  *A61B 5/00*    (2006.01)
  *G01R 33/28*   (2006.01)
  *A61B 5/055*   (2006.01)
  *G01R 33/30*   (2006.01)

(52) U.S. Cl.
  CPC .......... *A61B 5/7445* (2013.01); *A61B 5/0555* (2013.01); *A61B 5/7435* (2013.01); *G01R 33/283* (2013.01)

(58) Field of Classification Search
  CPC ... A61B 5/7445; A61B 5/0555; A61B 5/7435; A61B 6/04; G01R 33/283; A61G 13/12; G01B 33/44; G01B 33/48
  See application file for complete search history.

(56) References Cited

U.S. PATENT DOCUMENTS

| 5,134,373 | A  | * | 7/1992  | Tsuruno   | G01R 33/283 324/309 |
| 7,215,120 | B2 | * | 5/2007  | Vaughan   | G01R 33/283 324/318 |
| 7,537,184 | B1 | * | 5/2009  | Basilicato | G03B 21/54 248/123.11 |
| 2002/0148985 | A1 | * | 10/2002 | Takahashi | G01N 21/89 250/559.45 |

(Continued)

FOREIGN PATENT DOCUMENTS

| KR | 10-1004965 B1    | 1/2011 |
| KR | 10-2013-0027656 A | 3/2013 |
| KR | 10-2014-0058313 A | 5/2014 |

OTHER PUBLICATIONS

Communication dated Feb. 24, 2016, issued by the Korean Intellectual Property Office in counterpart Korean Application No. 10-2014-0090804.

(Continued)

*Primary Examiner* — Dixomara Vargas
*Assistant Examiner* — Zannatul Ferdous
(74) *Attorney, Agent, or Firm* — Sughrue Mion, PLLC

(57) ABSTRACT

Disclosed herein is a magnetic resonance imaging apparatus. The magnetic resonance imaging apparatus includes a table disposed in a cavity which is formed in a bore, a head support having a support hole through which an upper surface of the table is visible to an object disposed on the table, and a display configured to display a graphical user interface (GUI) image, the display being disposed between the table and the head support.

23 Claims, 23 Drawing Sheets

(56) References Cited

U.S. PATENT DOCUMENTS

| | | | | |
|---|---|---|---|---|
| 2005/0057542 A1* | 3/2005 | Plut | ............... | H04N 9/3141 345/204 |
| 2008/0306377 A1* | 12/2008 | Piron | ............... | A61B 8/0825 600/422 |
| 2009/0240150 A1* | 9/2009 | Wang | ............... | A61B 6/463 600/443 |
| 2013/0218004 A1* | 8/2013 | Yang | ............... | G01R 33/283 600/415 |
| 2013/0314303 A1* | 11/2013 | Osterhout | ............... | G06F 3/005 345/8 |

OTHER PUBLICATIONS

Communication dated Oct. 16, 2015, issued by the Korean Intellectual Property Office in corresponding Korean Application No. 10-2014-0090804.

* cited by examiner

MAGNETIC RESONANCE IMAGING APPARATUS

CROSS-REFERENCE TO RELATED APPLICATION(S)

This application claims priority from Korean Patent Application No. 10-2014-0090804, filed on Jul. 18, 2014 in the Korean Intellectual Property Office, the disclosure of which is incorporated herein by reference in its entirety.

BACKGROUND

1. Field

Exemplary embodiments relate to a magnetic resonance imaging apparatus displaying an image in a bore.

2. Description of the Related Art

In general, a medical imaging apparatus refers to an apparatus that provides an image with respect to a patient by acquiring information of the patient. Examples of the medical imaging apparatus include X-ray imaging apparatuses, ultrasonic diagnostic apparatuses, computed tomography (CT) scanners, magnetic resonance imaging (MRI) apparatuses, and the like.

Among these apparatuses, the magnetic resonance imaging apparatus holds a very important position in diagnosis using medical images due to relatively easy image capturing conditions, excellent contrast in soft tissue, and ability to provide various diagnosis information images thereof.

Magnetic resonance imaging (MRI) causes a nuclear magnetic resonance phenomenon to occur in hydrogen atomic nuclei in a human body by using a magnetic field which is harmless to the human body and a radio frequency (RF), which is non-ionizing radiation, to obtain density and physicochemical properties of the atomic nuclei which are illustrated in images.

In particular, a magnetic resonance imaging apparatus acquires an image of an inner portion of an object by converting energy, which is emitted from atomic nuclei in response to a supply of a constant frequency and energy while a constant magnetic field is applied to the inside of a gantry, into a signal.

In this case, an RF reception coil is used to receive the energy emitted from the atomic nuclei. The RF reception coil may be separated from a patient table. In general, the RF reception coil may be stored separately from the patient table while a magnetic resonance imaging process is not performed, and may be connected to the patient table while a magnetic resonance imaging process is being performed.

SUMMARY

Therefore, it is an aspect of one or more exemplary embodiments to provide a magnetic resonance imaging apparatus which facilitates an ability of an object to see a displayed image while the object is lying prone facing the table.

Additional aspects will be set forth in part in the description which follows and, in part, will be obvious from the description, or may be learned by practice of the exemplary embodiments.

In accordance with one aspect of one or more exemplary embodiments, a magnetic resonance imaging apparatus includes a table disposed in a cavity which is formed in a bore, a head support having a support hole through which an upper surface of the table is visible to an object disposed on the table, and a display configured to display a graphical user interface (GUI) image, the display being disposed between the table and the head support.

The display may include a projector configured to project the GUI image and a screen on which the GUI image projected by the projector is displayed.

The projector may be further configured to project the GUI image onto a back surface or a front surface of the screen.

The display may further include a mirror configured to reflect the GUI image projected by the projector toward the screen, and the projector may be further configured to project the GUI image onto the mirror such that the GUI image is reflected by the mirror onto the screen.

The magnetic resonance imaging apparatus may further include a guide configured to facilitate a vertical movement of the projector, and the screen may be configured to vertically move in accordance with a changing position of the projector. The guide may also have a curved shape.

The projector may be disposed on the table or off of the table, and the projector may be detachably disposed on the head support.

The display may include a display device on which the GUI image is displayed and a mirror configured to reflect the displayed image toward eyes of the object.

The display may include a projector configured to project the GUI image and a pair of glasses on which the image projected by the projector is formed.

The display may include a display on which the GUI image is displayed and a pair of glasses configured to reflect the image displayed on the display toward eyes of the object.

The magnetic resonance imaging apparatus may further include a darkroom housing configured to control a brightness between the table and the head support.

The magnetic resonance imaging apparatus may further include an input device configured to facilitate a control of the displayed GUI image.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
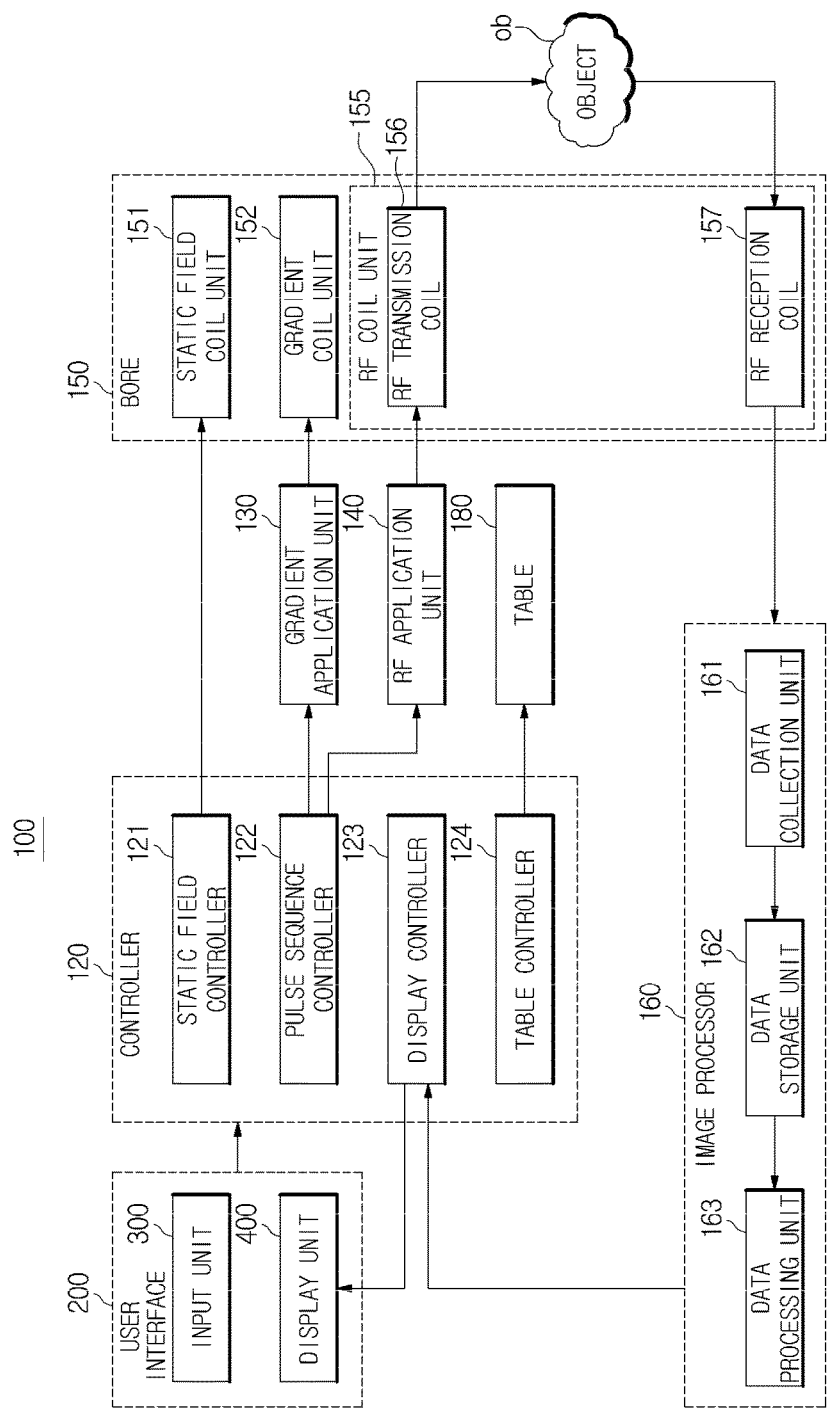
FIG. 1 is a block diagram illustrating a magnetic resonance imaging apparatus, according to an exemplary embodiment.

Reference will now be made in detail to exemplary embodiments, examples of which are illustrated in the accompanying drawings, wherein like reference numerals refer to like elements throughout. However, known functions associated with the exemplary embodiments or detailed descriptions on the configuration and other matters which would unnecessarily obscure the gist of the present disclosure will be omitted.

Further, the following terms, which are defined in consideration of functions of the exemplary embodiments, may be altered depending on the user's intentions or judicial precedents. Therefore, the meaning of each term should be interpreted based on the content of the entire disclosure of the specification. If there is no specific definition, the terms should be interpreted as generally interpreted by one of ordinary skill in the art.

Unless defined otherwise, all constituent elements according to aspects of the present disclosure and exemplary embodiments may be combined with each other, if it is obvious to one of ordinary skill in the art that combinations thereof are not technically contradictory, although a single integrated configuration thereof is illustrated in the drawings.

Hereinafter, magnetic resonance imaging apparatuses according to exemplary embodiments will be described with reference to the drawings.

Hereinafter, a magnetic resonance imaging apparatus according to an exemplary embodiment will be described with reference to FIGS. 1 and 2.

FIG. 1 is a block diagram illustrating a configuration of a magnetic resonance imaging apparatus 100.

Referring to FIG. 1, the magnetic resonance imaging apparatus 100 includes a bore 150, a controller 120, a gradient application unit (also referred to herein as a "gradient application device") 130, an RF application unit (also referred to herein as an "RF application device") 140, an image processor 160, and a support.

The bore 150 forms a magnetic field and generates a resonance phenomenon with respect to atomic nuclei.

In particular, the bore 150 includes a static field coil unit (also referred to herein as a "static field coil device") 151 configured to generate a static magnetic field in an inner space thereof, a gradient coil unit (also referred to herein as a "gradient coil device") 152 configured to form a gradient magnetic field by generating a gradient in the static magnetic field, and a radio frequency (RF) coil unit (also referred to herein as an "RF coil device") 155 configured to excite the atomic nuclei by applying RF pulses and to receive echo signals from the atomic nuclei.

When an object ob is located in an inner space of the bore 150 of the magnetic resonance imaging apparatus 100, a static magnetic field, a gradient magnetic field, and RF pulses may be applied to the object ob. In addition, the atomic nuclei which are contained in the object ob are excited by the applied RF pulses, and echo signals are generated therefrom.

The RF coil unit 155 may include an RF transmission coil 156 configured to excite atomic nuclei by applying RF pulses and an RF reception coil 157 configured to receive echo signals generated by the bore 150 and to transmit the received echo signals to the image processor 160.

The RF reception coil 157 may receive electromagnetic waves emitted from the excited atomic nuclei, i.e., magnetic resonance signals. The RF reception coil 157 is generally used in a state of being attached to a human body. Thus, the RF reception coil 157 may have any of various shapes in accordance with parts of the human body, such as, for example, a head coil, a neck coil, and a waste coil.

As an example of the RF reception coil 157 that may be separated from the bore 150, a surface coil receives magnetic resonance signals which are excited in a part of the object ob. Since the surface coil is smaller than a volume coil and has a two-dimensional sheet shape, the surface coil has a relatively high signal-to-noise ratio with respect to an adjacent portion.

In addition, as another example of the RF reception coil 157, an array coil has a wide reception area which results from an alignment of a plurality of surface coils in a one-dimensional or two-dimensional space. The array coil has a respective alignment shape in accordance with body parts to be examined, and may be classified into array coils for head, array coils for head and neck, array coils for chest, array coils for spine, array coils for abdomen, and array coils for leg. Since the surface coils constituting the array coil have different relative positions, signals received by the surface coils have different phases. Thus, an image having a relatively high signal-to-noise ratio may be acquired by considering a receive phase of each of the surface coils while reconstructing an image by combining the signals received by respective surface coils.

The controller 120 includes a static field controller 121 configured to control an intensity and a direction of the static magnetic field formed by the static field coil unit 151, a pulse sequence controller 122 configured to design a pulse sequence and to control the gradient coil unit 152 and the RF coil unit 155 in accordance with the pulse sequence, a display controller 123 configured to control a graphical user interface (GUI) image displayed on a display unit (also referred to herein as a "display" and/or as a "display device") 400, and a table controller 124 configured to control a position of a table 180.

The controller 120 may function as a central processing unit (CPU), and the CPU may include a microprocessor. The microprocessor is a processing device which includes an arithmetic logic unit, a register, a program counter, an instruction decoder, and/or a control circuit, and the like integrated in at least one silicon chip.

Further, the microprocessor may include a graphic processing unit (GPU) configured for graphical processing of an image and/or video. The microprocessor may be implemented in a System-on-Chip (SoC) which includes a core and a GPU. The microprocessor may include any of a single core processor, a dual core processor, a triple core processor, a quad core processor, and a multi core processor.

In addition, the controller 120 may include any of a graphic processing board fabricated by disposing a GPU, a random access memory (RAM), and/or a read-only memory (ROM) in a separate circuit board which is electrically connected to the microprocessor.

The magnetic resonance imaging apparatus 100 includes a gradient application unit (also referred to herein as a "gradient application device) 130 configured to apply a gradient signal to the gradient coil unit 152 and an RF application unit (also referred to herein as an "RF application device") 140 configured to apply an RF signal to the RF transmission coil 156. The pulse sequence controller 122 controls the gradient application unit 130 and the RF application unit 140 to control the gradient magnetic field formed in the inner space of the bore 150 and RF signals applied to the atomic nuclei.

The magnetic resonance imaging apparatus 100 includes the image processor 160 which is configured to generate a magnetic resonance image based on the echo signals generated in the atomic nuclei, i.e., magnetic resonance signals.

The RF reception coil 157 is connected to the image processor 160. The image processor 160 may include a data collection unit (also referred to herein as a "data collector") 161 configured to generate a magnetic resonance image by receiving data regarding spin echo signals, i.e., magnetic resonance signals generated in the atomic nuclei, and processing the received data, a data storage unit (also referred to herein as a "data storage" and/or as a "data storage device") 162 configured to store the data received by the data collection unit 161, and a data processing unit (also referred to herein as a "data processor") 163 configured to generate a magnetic resonance image by processing the stored data.

The data collection unit 161 may include a preamplifier configured to amplify magnetic resonance signals received by the RF coil unit 155, a phase detector configured to detect a phase upon receiving the magnetic resonance signals from the preamplifier, and an A/D converter configured to convert analog signals acquired by the phase detection into digital signals. In addition, the data collection unit 161 transmits the magnetic resonance signals, which are converted into the digital signals, to the data storage unit 162.

In the data storage unit 162, a data space constituting a two-dimensional Fourier space is formed. When the scanned entire data is completely stored, the data processing unit 163 reconstructs an image of the object ob by performing a two-dimensional inverse Fourier transform of the data within the two-dimensional Fourier space. The reconstructed image is transmitted to the display controller 123, and the display controller 123 displays the reconstructed image on the display unit 400.

The magnetic resonance imaging apparatus 100 may include a user interface 200 configured to receive control instructions regarding the overall operation of the magnetic resonance imaging apparatus 100 which are inputted by the user. In particular, a pulse sequence may be generated in accordance with an instruction regarding a scan sequence received from the user.

In particular, the user interface 200 may include an input unit (also referred to herein as an "input device") 300 configured to enable the user to manipulate a system and a display unit (also referred to herein as a "display" and/or as a "display device") 400 configured to enable the user to diagnose the health condition of the object ob by displaying a control state and an image generated by the image processor 160.

The input unit 300 will be described in detail below with reference to FIG. 16.

The display unit 400 may include a projector 410, a display 420, a mirror 430, a screen 440, and glasses 450.

The display unit 400 will be described in detail below with reference to FIGS. 4 to 14B.

The support supports the body of the object ob when the object ob is located on the table 180 for magnetic resonance imaging.

In addition, the support may include a head support 500, a chest support 510, and an abdomen support 520.

The support will be described in detail below with reference to FIG. 3.

The magnetic resonance imaging apparatus 100 may also include a memory. The memory may store any one or more of a magnetic resonance image of the object ob, an echo signal received from the object ob, and/or a particular value with respect to soft tissues. The memory may also store any of various data used to control the magnetic resonance imaging apparatus 100. For example, the memory may store data regarding the control of performing a magnetic resonance imaging for a biopsy, moving the table 180 out of the bore 150 for an invasive procedure with respect to soft tissues of the object ob, and moving the table 180 into the bore 150 after the invasive procedure.

The memory may include non-volatile memory such as any of a read-only memory (ROM), a high-speed random access memory (RAM), a magnetic disk storage device, and a flash memory, and/or any other non-volatile semiconductor memory devices.

For example, the memory may include semiconductor memory devices such as any one or more of a secure digital (SD) memory card, a secure digital high capacity (SDHC) memory card, a mini SD memory card, a mini SDHC memory card, a trans flash (TF) memory card, a micro SD memory card, a micro SDHC memory card, a memory stick, a compact flash (CF) memory card, a multi-media card (MMC), an MMC micro card, and/or an extreme digital (XD) card.

In addition, the memory may include a network-attached storage device which is configured to access files via a network.

Figure 2:
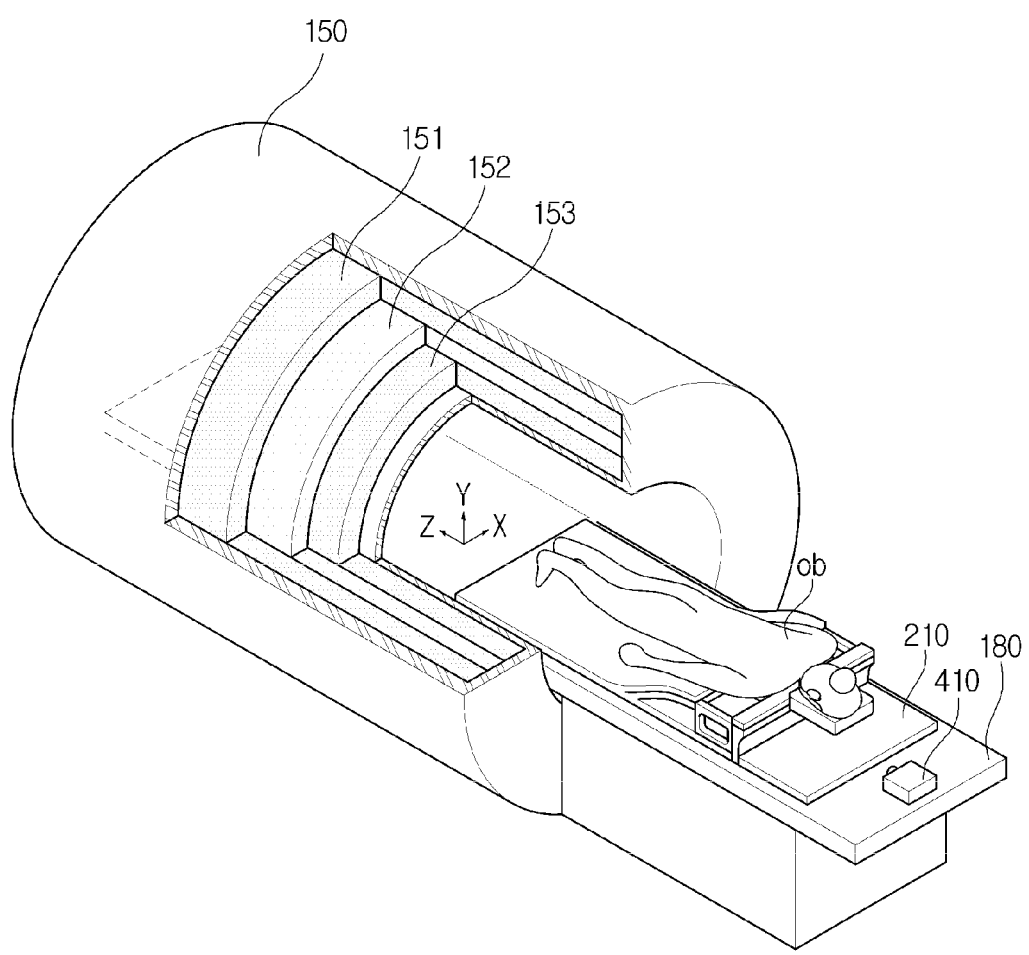
FIG. 2 is a perspective view illustrating a magnetic resonance imaging apparatus, according to an exemplary embodiment.

FIG. 2 illustrates an external appearance of the magnetic resonance imaging apparatus.

Referring to FIG. 2, the bore 150 is formed in the shape of a cylinder having a hollow inner space, and may also be referred to as a gantry. The inner space is referred to as a cavity, and an object ob lying on the table 180 is brought into the cavity in order to obtain a magnetic resonance signal.

The bore 150 may include the static field coil unit 151, the gradient coil unit 152, and the RF coil unit 155.

The static field coil unit 151 may be configured by winding a coil around the cavity. When current is supplied to the static field coil unit 151, a static magnetic field is formed in the inner space of the bore 150, i.e., the cavity.

Generally, a direction of the static magnetic field is parallel to an axis of the bore 150.

When the static magnetic field is formed in the cavity, nuclei of atoms constituting the object ob, most particularly including nuclei of hydrogen atoms, are arranged in the direction of the static magnetic field, and perform a procession about the direction of the static magnetic field. Procession speed of the atomic nuclei may be expressed by precession frequency. The precession frequency is referred to as Larmor frequency, which is represented by Equation 1.

$$\omega = \gamma B0 \qquad \text{Equation 1}$$

In Equation 1, $\omega$ is a Larmor frequency, $\gamma$ is a proportional constant, and B0 is intensity of an external magnetic field. The proportional constant varies according to the type of atomic nuclei. A unit of the intensity of the external magnetic field is tesla (T) or gauss (G), and a unit of the precession frequency is Hz.

For example, a hydrogen proton has a precession frequency of 42.58 MHZ in an external magnetic field of 1 T. Since hydrogen occupies the greatest proportion among atoms constituting the human body, the magnetic resonance imaging apparatus 100 obtains magnetic resonance signals by using procession of hydrogen protons.

The gradient coil unit 152 generates a gradient magnetic field by causing a gradient in the static magnetic field formed in the cavity.

Hereinafter, a magnetic resonance imaging apparatus 100 according to an exemplary embodiment will be described with reference to FIG. 3.

Figure 3:
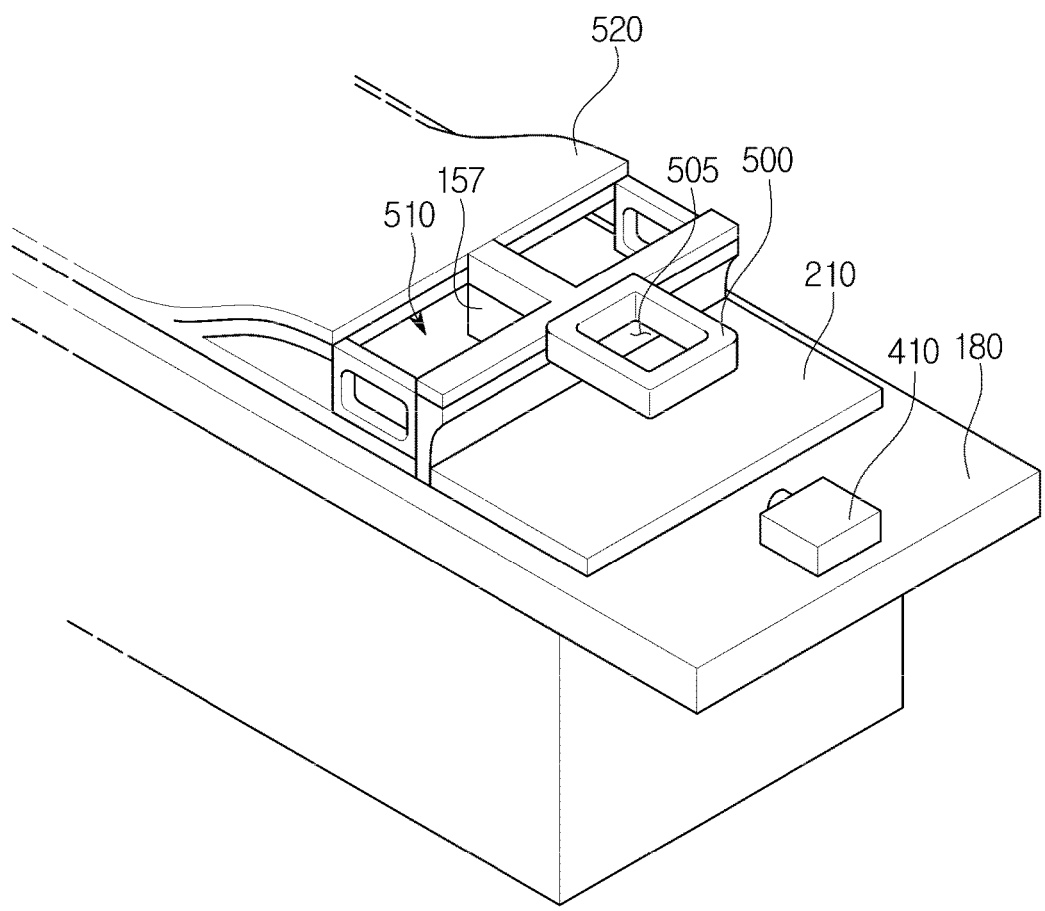
FIG. 3 is a perspective view illustrating an RF coil unit, a head support, and a projector, according to an exemplary embodiment.

FIG. 3 illustrates external appearances of an RF coil unit 155, a head support 500, and a projector 410.

The magnetic resonance imaging apparatus 100 may include a projector 410, an RF reception coil 157, and a support.

The projector 410 and the RF reception coil 157 may be the same as or different from the projector 410 and the RF reception coil 157 of FIG. 1.

The support provides a supporting space such that the object ob is supported in a position adjacent to the RF reception coil 157 for magnetic resonance imaging.

In particular, the support provides the supporting space such that the object ob lies prone facing the table 180. In addition, the support may include a head support 500, a chest support 510, and an abdomen support 520.

The head support 500 supports the face of the object ob. In particular, the head support 500 has a supporting hole 505 at the center where the face of the object ob is positioned and a supporting structure at a circumferential area of the supporting hole 505 to support the face of the object ob. The supporting structure may include a cushion which is intended to relieve pain of the object ob.

In addition, the object ob may be able to see a GUI image displayed below the head support 500 through the supporting hole 505 of the head support 500.

The chest support 510 is disposed near the RF reception coil 157 and is configured to provide spaces for accommodating breasts of the object ob. In particular, the chest support 510 includes a barrier wall and has spaces allowing breasts to hang at both sides of the barrier wall. In addition, supporting frames may be disposed at outer portions thereof. The supporting frames may press the breasts from the outside while imaging the breasts of the object ob so as to reduce movement of regions to be diagnosed.

The abdomen support 520, which is disposed at a position adjacent to the chest support 510 and opposite to the head support 500, supports the abdomen of the object ob. In particular, the abdomen support 520 may have a slope which is configured to support the abdomen of the object ob when the object ob positions the breasts in the chest support 510 and the head in the head support 500 in a state of lying prone. In addition, the abdomen support 520 may have a slightly curved surface in correspondence to a shape of the body of the object ob. In addition, the abdomen support 520 may include a cushion formed of a soft material in order to relieve pain of the object ob in the same manner as the head support 500.

Hereinafter, a method for displaying a GUI image by using a projector according to an exemplary embodiment will be described with reference to FIGS. 4, 5A, and 5B.

Figure 4:
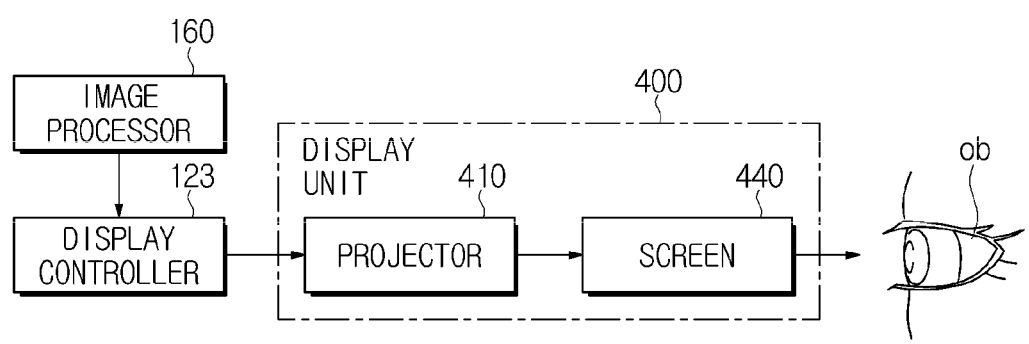
FIG. 4 is a block diagram illustrating a configuration of displaying a GUI image, according to an exemplary embodiment.

FIG. 4 is a block diagram illustrating a configuration of displaying a GUI image.

An image processor 160 generates a magnetic resonance image based on echo signals and transmits the generated magnetic resonance image to a display controller 123, and the display controller 123 transmits a control signal to a display unit 400 and controls the display unit 400 to display an image such that the object ob is able to see a GUI image.

According to the exemplary embodiment illustrated in FIG. 4, the display unit 400 may include a projector 410 and a screen 440. In addition, the display unit 400 may display a GUI image between the head support 500 and the table 180. The GUI image may show not only the magnetic resonance image, but also any one or more of a remaining time of the magnetic resonance imaging process, an image which provides a caution against movement, an image or text regarding the current status, and/or the like.

The projector 410, as a projection device, is a device which is configured to display a slide or video image by using light. The projector 410 may project light beams onto a screen 440 in a state of being disposed on the table 180 or from outside of the magnetic resonance imaging apparatus.

The screen 440 is a place where the GUI image is formed by the light beams projected by the projector 410 and diffused and/or reflected. The screen 440 may include an opaque screen 444 and a transparent screen 448.

In particular, the screen 440 may be classified into the opaque screen 444 and the transparent screen 448. When the opaque screen 444 is used, the object ob cannot see the table 180 through the supporting hole 505 of the head support 500. However, when the transparent screen 448 is used, the object ob may see the table 180 through the supporting hole 505 of the head support 500.

The opaque screen 444 has a non-uniform surface which causes a diffused reflection of light beams projected by the projector 410 and may include a material having a brightness and a chroma similar to those of white color in order to improve visibility.

Conversely, the transparent screen 448 includes a plastic film therein which is configured for diffused reflection and regular reflection, and the plastic film may be a wedge type. In addition, plate glasses may be disposed on both external sides of the plastic film.

The screen 440 may be formed of any of various materials according to the type of light beams projected by the projector 410. For example, when an image is displayed via front projection, the opaque screen 444 may be a Matt White screen, a Glass-beaded screen, a Ultra-Beaded screen, and/or a Lenticular screen. Conversely, when an image is displayed by backward projection, Cineflex may be used.

Hereinafter, external appearances of the magnetic resonance imaging apparatuses according to the exemplary embodiment illustrated in FIG. 4 will be described with reference to FIGS. 5A and 5B.

Figure 5A:
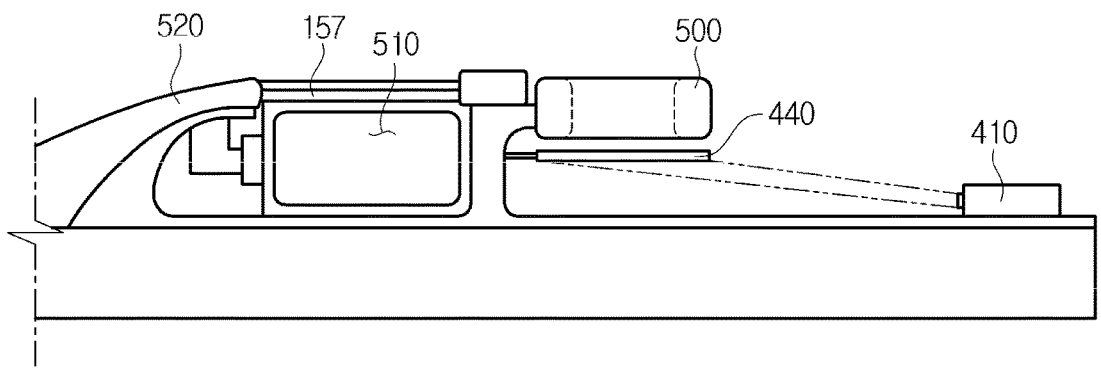
FIG. 5A is a cross-sectional view of a magnetic resonance imaging apparatus, according to the exemplary embodiment illustrated in FIG. 4, illustrating an example of displaying an image by using a projector disposed on a table.

FIG. 5A illustrates an example of displaying an image by using a projector disposed on a table. FIG. 5B illustrates an example of displaying an image by using a projector disposed on a head support.

Figure 5B:
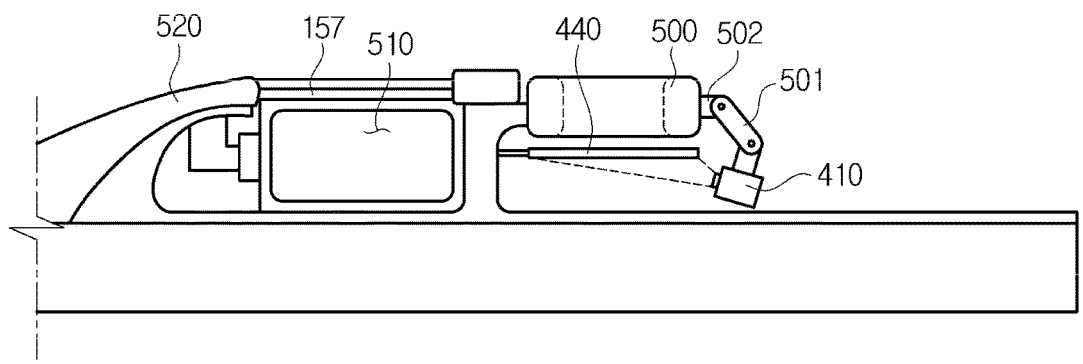
FIG. 5B is a cross-sectional view of the magnetic resonance imaging apparatus, according to the exemplary embodiment illustrated in FIG. 4, illustrating an example of displaying an image by using a projector disposed on a head support.

As illustrated in FIGS. 5A and 5B, in the magnetic resonance imaging apparatus 100, the abdomen support 520, the chest support 510, and the head support 500 are sequentially disposed, and the table 180 is disposed below the bottom surface of the support. A GUI image is displayed between the head support 500 and the table 180.

In particular, according to the exemplary embodiment illustrated in FIG. 4, the screen 440 is disposed between the head support 500 and the table 180 for backward projection, and the GUI image may be formed on the screen 440.

The image displayed on the screen 440 is formed by light beams projected by the projector 410. In the magnetic resonance imaging apparatus 100 according to the exemplary embodiment illustrated in FIG. 4, the projector 410 may be disposed at a position which is different from that of the screen 440.

In particular, as illustrated in FIG. 5A, the projector 410 may project light beams onto a back surface of the screen 440 in a state of being disposed on the table 180. Alternatively, as illustrated in FIG. 5B, the projector 410 may project light beams onto the back surface of the screen 440 in a state of being connected to a connection arm disposed on the head support 500.

In addition, if required, the projector 410 may be detachable for image capturing. In particular, the connection arm of FIG. 5B may include a detachable arm 502 and a fixing arm 501. In this regard, the detachable arm 502, which functions as a connector, may be detachably connected to the head support 500, and the fixing arm 501 may fix and support the projector 410 in a state of being connected to the detachable arm 502.

Hereinafter, a method for displaying a GUI image by using a projector according to another exemplary embodiment will be described with reference to FIGS. 6 to 10.

Figure 6:
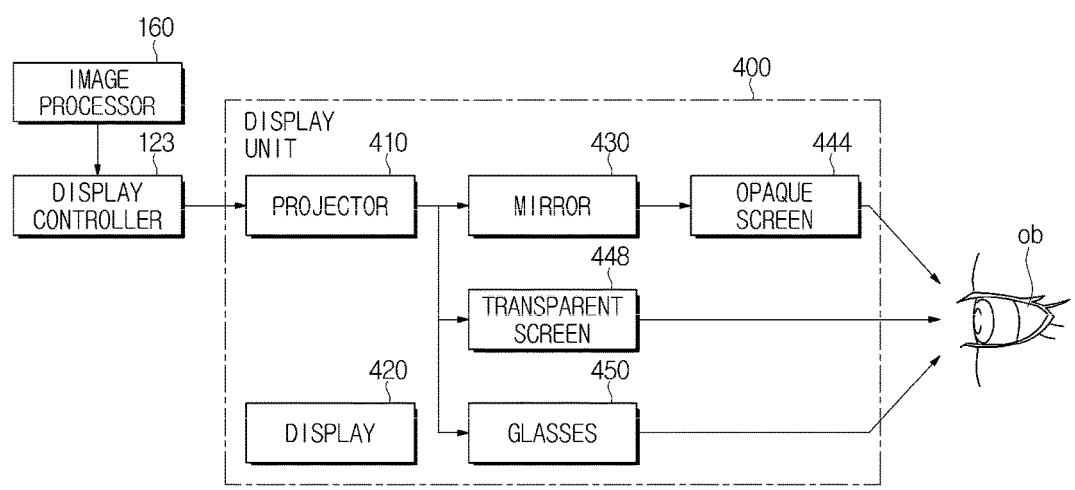
FIG. 6 is a block diagram illustrating a configuration of displaying a GUI image, according to another exemplary embodiment.

FIG. 6 is a block diagram illustrating a configuration of displaying a GUI image.

An image processor 160 generates a magnetic resonance image based on echo signals and transmits the generated magnetic resonance image to a display controller 123, and the display controller 123 transmits a control signal to a display unit 400 and controls the display unit 400 to display an image such that a GUI image is visible to the object ob.

According to the exemplary embodiment illustrated in FIG. 6, the display unit 400 may include a projector 410, a screen 440, a mirror 430, and a pair of glasses 450. In addition, the display unit 400 according to the exemplary embodiment illustrated in FIG. 6 may be the same as or different from the display unit 400 according to the exemplary embodiment illustrated in FIG. 4.

The projector 410 and the screen 440 according to the exemplary embodiment illustrated in FIG. 6 may be the same or different from the projector 410 and the screen 440 according to the exemplary embodiment illustrated in FIG. 4.

The mirror 430 may change a path of light beams projected by the projector 410 and transmit the light beams to the screen 440. In addition, the mirror 430 may have a flat surface or a curved surface. The mirror 430 may also have a convex shape, a concave shape, or a flat shape, in accordance with a width of incident light beams, a distance to the screen 440, and a width of the screen 440.

The glasses 450 are supported by the head of the object ob, and a GUI image may be formed near eyes of the object ob. The glasses 450 will be described in more detail below with reference to FIGS. 13A and 13B.

Hereinafter, external appearances of display units according to the exemplary embodiment illustrated in FIG. 6 respectively transmitting light beams, which are projected in a direction which is parallel to a surface of a table, to a screen by using a mirror will be described with reference to FIGS. 7A and 7B.

Figure 7A:
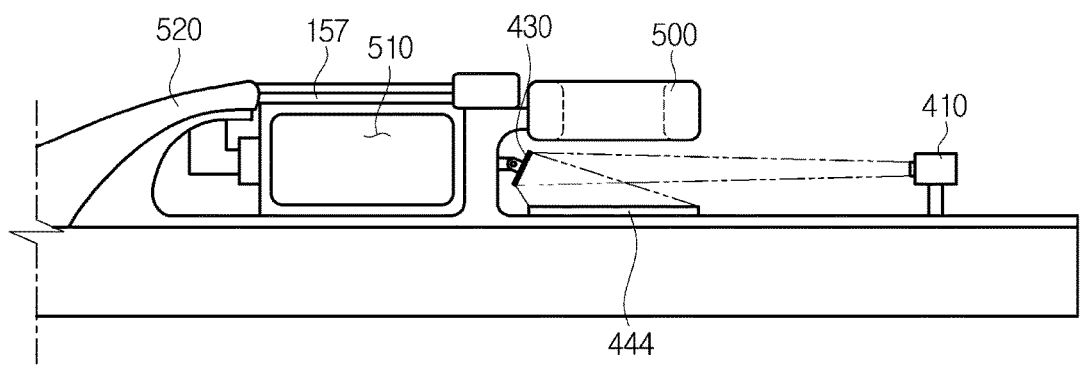
FIG. 7A is a cross-sectional view of the magnetic resonance imaging apparatus, according to the exemplary embodiment illustrated in FIG. 6, illustrating an example of displaying an image by using a projector disposed on a table and a mirror.

FIG. 7A illustrates an example of displaying an image by using a projector disposed on a table and a mirror. FIG. 7B illustrates an example of displaying an image by using a projector disposed on a head support and a mirror.

Figure 7B:
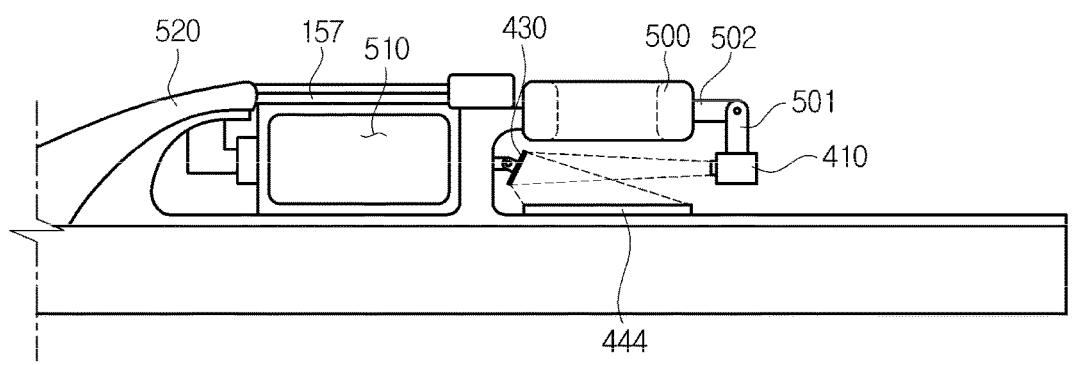
FIG. 7B is a cross-sectional view of the magnetic resonance imaging apparatus, according to the exemplary embodiment illustrated in FIG. 6, illustrating an example of displaying an image by using a projector disposed on a head support and a mirror.

As illustrated in FIGS. 7A and 7B, in the magnetic resonance imaging apparatus 100, the abdomen support 520, the chest support 510, and the head support 500 are sequentially disposed, and the mirror 430 and the table 180 are disposed below the bottom surface of the support. A GUI image is displayed between the head support 500 and the table 180.

In particular, light beams incident on the mirror 430 in a direction parallel to the table 180 is regular-reflected and transmitted to the screen 440, and the light beams transmitted to the screen 440 are diffused-reflected on the screen 440, thereby forming the GUI image.

In addition, in the magnetic resonance imaging apparatus 100 according to the exemplary embodiment illustrated in FIG. 6, the projector 410 may be disposed at a position which is different from that of the screen 440.

In particular, as illustrated in FIG. 7A, the projector 410 may project light beams onto the mirror 430 in a state of being disposed on the table 180. Alternatively, the projector 410 may project light beams onto the mirror 430 in a state of being connected to the connection arm which is disposed on the head support 500, as illustrated in FIG. 7B.

The projector 410 may also be detachable for image capturing, if required. In particular, the connection arm of FIG. 7B may include a detachable arm 502 and a fixing arm 501. In this regard, the detachable arm 502 functioning as a connector may be detachably connected to the head support 500, and the fixing arm 501 may fix and support the projector 410 in a state of being connected to the detachable arm 502.

Hereinafter, external appearances of display units according to the exemplary embodiment illustrated in FIG. 6 respectively transmitting light beams, which are projected in a direction parallel to a table, to a screen without using a mirror will be described with reference to FIGS. 8A and 8B.

Figure 8A:
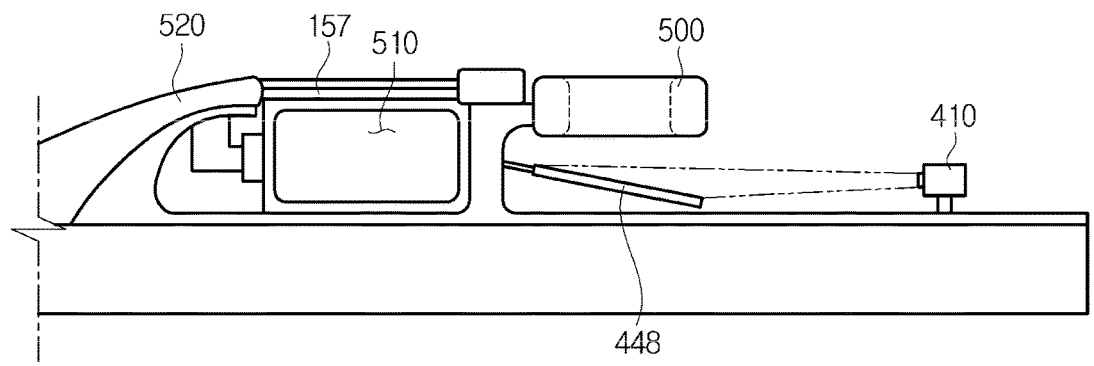
FIG. 8A is a cross-sectional view of the magnetic resonance imaging apparatus, according to the exemplary embodiment illustrated in FIG. 6, illustrating an example of displaying an image by horizontally projecting light beams by using a projector disposed on a table.

FIG. 8A illustrates an example of displaying an image by horizontally projecting light beams by using a projector disposed on a table. FIG. 8B illustrates an example of displaying an image by horizontally projecting light beams by using a projector disposed on a head support.

Figure 8B:
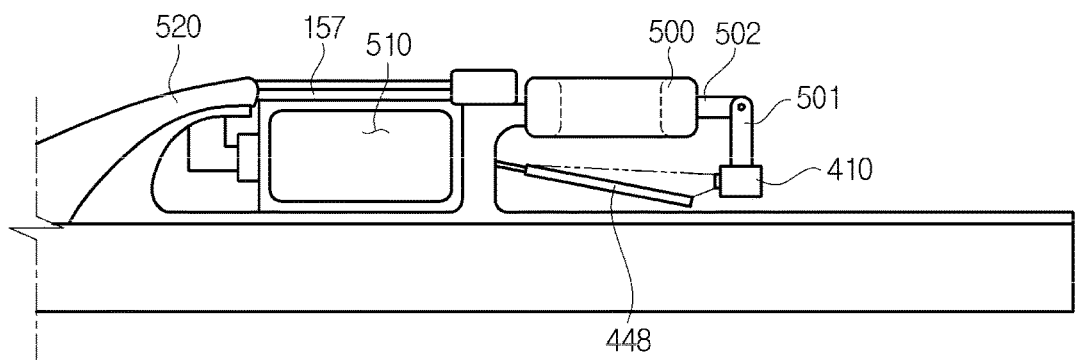
FIG. 8B is a cross-sectional view of the magnetic resonance imaging apparatus, according to the exemplary embodiment illustrated in FIG. 6, illustrating an example of displaying an image by horizontally projecting light beams by using a projector disposed on a head support.

As illustrated in FIGS. 8A and 8B, in the magnetic resonance imaging apparatus 100, the abdomen support 520, the chest support 510, and the head support 500 are sequentially disposed, and the table 180 is disposed below the bottom surface of the support. A GUI image is displayed between the head support 500 and the table 180.

In particular, the screen 440 is disposed so as to be nonparallel to the table 180 and has a slope toward the projector 410. Light beams incident on the screen 440 parallel to table 180 from the projector 410 are diffused-reflected on the screen 440 to form a GUI image.

In addition, in the magnetic resonance imaging apparatus 100 according to the exemplary embodiment illustrated in FIG. 6, the projector 410 may be disposed at a position which is different from that of the screen 440.

In particular, as illustrated in FIG. 8A, the projector 410 may project light beams onto a front surface of the screen 440 in a state of being disposed on the table 180. Alternatively, as illustrated in FIG. 8B, the projector 410 may project light beams onto the front surface of the screen 440 in a state of being connected to the connection arm which is disposed on the head support 500.

In addition, if required, the projector 410 may be detachable for image capturing. Particularly, the connection arm of FIG. 8B may include a detachable arm 502 and a fixing arm 501. In this regard, the detachable arm 502 which functions as a connector may be detachably connected to the head support 500, and the fixing arm 501 may fix and support the projector 410 in a state of being connected to the detachable arm 502.

Hereinafter, external appearances of display units according to the exemplary embodiment illustrated in FIG. 6 respectively directly transmitting light beams, which are projected downward in an oblique direction from a position above a table, to a screen will be described with reference to FIGS. 9A and 9B.

Figure 9A:
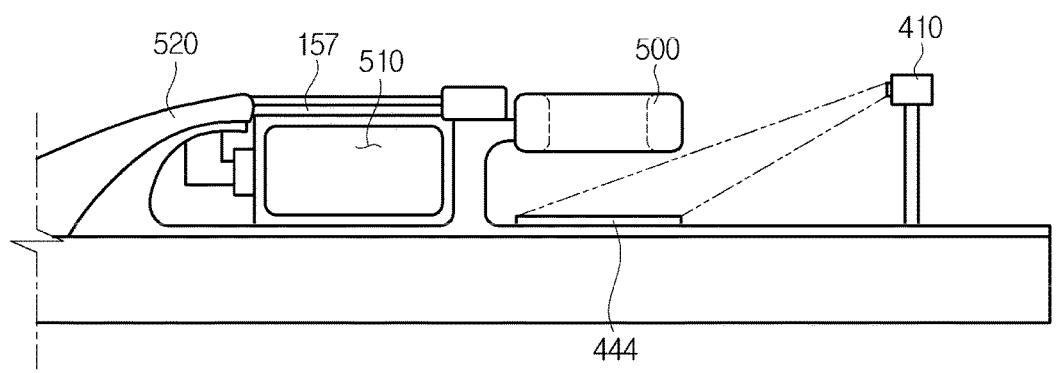
FIG. 9A is a cross-sectional view of the magnetic resonance imaging apparatus, according to the exemplary embodiment illustrated in FIG. 6, illustrating an example of displaying an image by projecting light beams downward by using a projector disposed on a table.

FIG. 9A illustrates an example of displaying an image by projecting light beams downward by using a projector disposed on a table. FIG. 9B illustrates an example of displaying an image by projecting light beams downward by using a projector disposed on a head support.

Figure 9B:
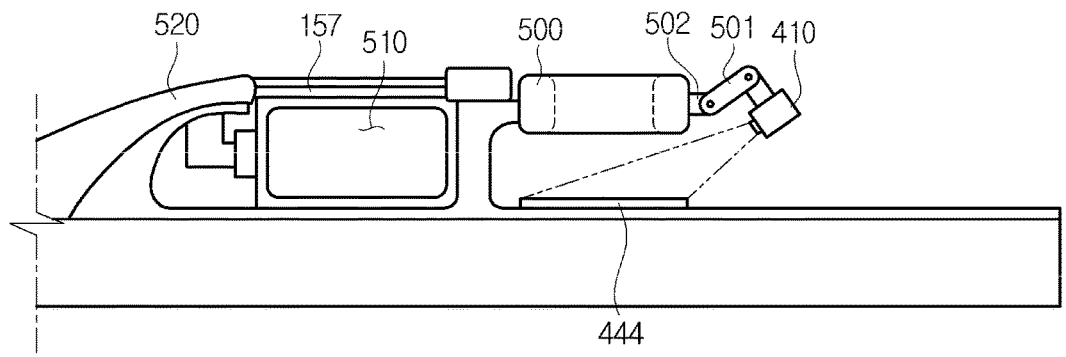
FIG. 9B is a cross-sectional view of the magnetic resonance imaging apparatus, according to the exemplary embodiment illustrated in FIG. 6, illustrating an example of displaying an image by projecting light beams downward by using a projector disposed on a head support.

As illustrated in FIGS. 9A and 9B, in the magnetic resonance imaging apparatus 100, the abdomen support 520, the chest support 510, and the head support 500 are sequentially disposed, and the table 180 is disposed below the bottom surface of the support. A GUI image is displayed between the head support 500 and the table 180.

In particular, the screen 440 is disposed near the table 180, so that light beams projected in an oblique direction toward the screen 440 are diffused-reflected on the screen 440, thereby forming the GUI image.

In addition, in the magnetic resonance imaging apparatus 100 according to the exemplary embodiment illustrated in FIG. 6, the projector 410 may be disposed at a position which is different from that of the screen 440.

In particular, as illustrated in FIG. 9A, the projector 410 may project light beams onto a front surface of the screen 440 in a state of being disposed on the table 180. Alternatively, the projector 410 may project light beams onto the front surface of the screen 440 in a state of being connected to the connection arm which is disposed on the head support 500 as illustrated in FIG. 7B.

The projector 410 may also be detachable for image capturing, if required. In particular, referring to FIG. 9B, the connection arm may include a detachable arm 502 and a fixing arm 501. In this regard, the detachable arm 502 which functions as a connector may be detachably connected to the head support 500, and the fixing arm 501 may fix and support the projector 410 in a state of being connected to the detachable arm 502.

Figure 10:
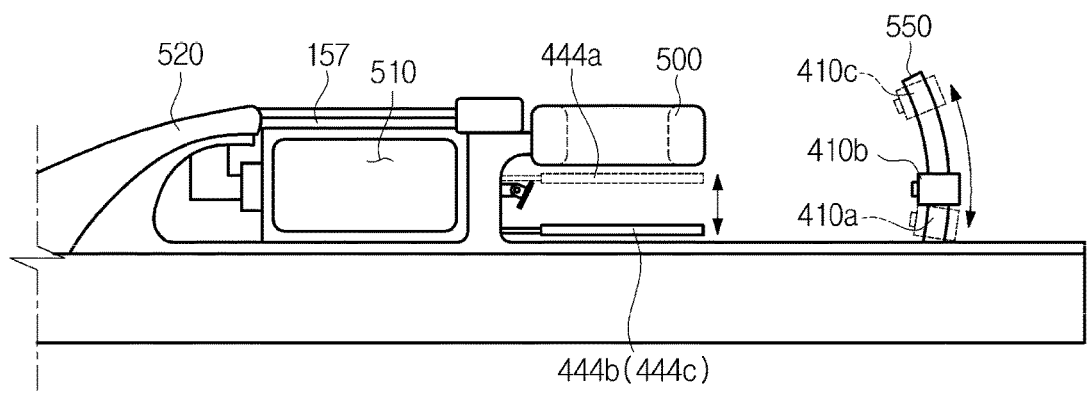
FIG. 10 is a cross-sectional view of the magnetic resonance imaging apparatus, according to the exemplary embodiment illustrated in FIG. 6, illustrating an example of displaying an image by vertically moving a projector by using a guide unit.

FIG. 10 illustrates an example of displaying an image by vertically moving a projector by using a guide unit (also referred to herein as a "guide") 550.

According to the exemplary embodiment illustrated in FIG. 10, the method for displaying an image by backward projection, the method for displaying an image by transmitting light beams incident in a direction parallel to the table 180 to the screen 440 by using the mirror 430, and the method for displaying an image by front projection of light beams in an oblique direction toward the table 180 as described above are performed by moving the projector 410 and the screen 440.

In particular, the screen 440 may vertically move between the table 180 and the head support 500, and the projector 410 may vertically move along the guide unit 550 as illustrated in FIG. 10.

The guide unit 550 may have a curved shape such that the center of curvature of the guide unit 550 is disposed at a screen 440 side. In addition, the guide unit 550 is disposed on the table 180 such that light beams projected by the projector 410 are incident onto the screen 440. In addition, the screen 440 may move in accordance with a position where the image is formed by light beams projected by the projector 410 moving along the guide unit 550.

In this aspect, in order to implement the method for displaying an image by backward projection, the screen 440*a* may be moved to be adjacent to the head support 500, and the projector 410*a* may be moved to a lower portion of the guide unit 550 in the magnetic resonance imaging apparatus 100, as illustrated in FIG. 10.

In order to implement the method for displaying an image by transmitting light beams incident in the direction parallel to the table 180 to the screen 440*b* by using the mirror 430, the screen 440*b* may be moved to be adjacent to the table 180, and the projector 410*b* may be moved to a middle portion of the guide unit 550 in the magnetic resonance imaging apparatus 100, as illustrated in FIG. 10.

In order to implement the method for displaying an image by front projection of light beams in an oblique direction toward the table, the screen 440*c* may be moved to be adjacent to the table 180, and the projector 410*c* may be moved to an upper portion of the guide unit 550 in the magnetic resonance imaging apparatus 100, as illustrated in FIG. 10.

Hereinafter, a method for displaying a GUI image by using a projector according to still another exemplary embodiment will be described with reference to FIGS. 11, 12A, and 12B.

Figure 11:
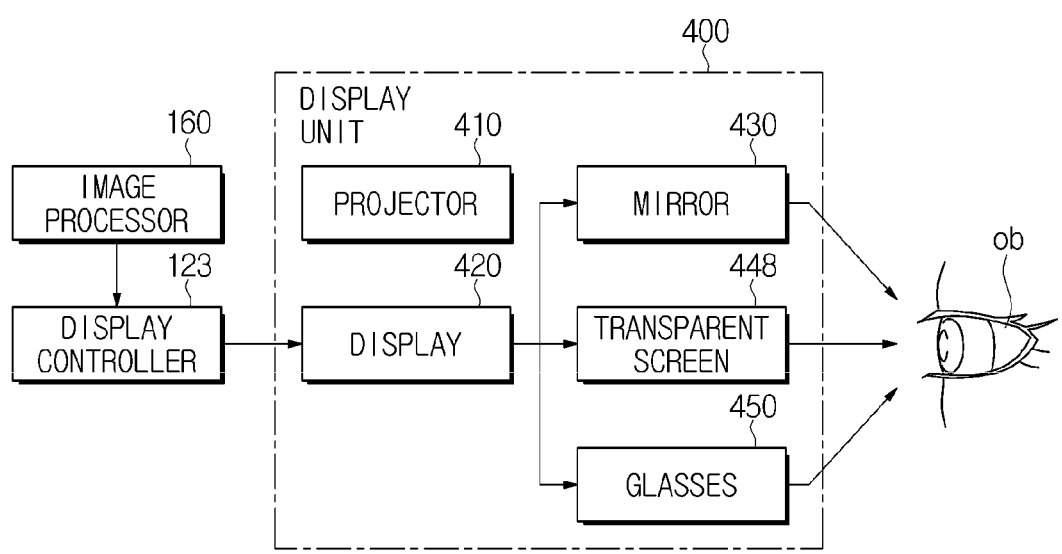
FIG. 11 is a block diagram illustrating a configuration of displaying a GUI image by reflection without forming an image, according to still another exemplary embodiment.

FIG. 11 is a block diagram illustrating a configuration of displaying a GUI image by reflection without forming an image.

An image processor 160 generates a magnetic resonance image based on echo signals and transmits the generated magnetic resonance image to a display controller 123, and the display controller 123 transmits a control signal to a display unit 400 and controls the display unit 400 to display an image such that the object ob is able to see a GUI image.

According to the exemplary embodiment illustrated in FIG. 11, the display unit 400 may include a display 420, a transparent screen 448, a mirror 430, and glasses 450. In addition, the display unit 400 according to the exemplary embodiment illustrated in FIG. 11 may be the same as or different from the display unit 400 according to the exemplary embodiment illustrated in FIG. 6.

The transparent screen 448, the mirror 430, and the glasses 450 according to the exemplary embodiment illustrated in FIG. 11 may be the same as or different from the transparent screen 448, the mirror 430, and the glasses 450 according to the exemplary embodiment illustrated in FIG. 6.

The mirror 430 may change a propagation path of light beams displayed on the display 420 and redirect the light beams to the screen 440. In addition, the mirror 430 may have a flat surface or a curved surface. The mirror 430 may also have a convex shape, a concave shape, or a flat shape, in accordance with a width of the display 420, a distance to the display 420, and/or a width of the display 420.

The glasses 450 are supported by the head of the object ob, and a GUI image displayed on the display 420 may be reflected by the glasses 450 and incident onto eyes of the object ob. The glasses 450 will be described in more detail below with reference to FIGS. 13A and 13B.

The display 420 displays the GUI image via light emission. In addition, in the display 420, any of light emitting diode (LED) technology, liquid crystal display (LCD) technology, and/or light emitting polymer display (LPD) technology may be used. Any other of various display technologies may also be applied to the display 420.

Hereinafter, external appearances of display units according to the exemplary embodiment illustrated in FIG. 11 respectively displaying an image to an object ob by using a mirror will be described with reference to FIGS. 12A and 12B.

Figure 12A:
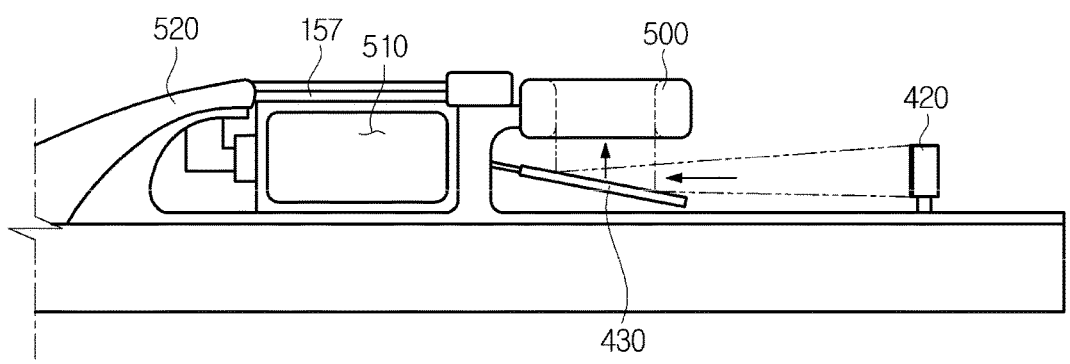
FIG. 12A is a cross-sectional view of the magnetic resonance imaging apparatus, according to the exemplary embodiment illustrated in FIG. 11, illustrating an example of displaying an image by using a display unit disposed on a table and a mirror.

FIG. 12A illustrates an example of displaying an image by using a display unit disposed on a table and a mirror. FIG. 12B illustrates an example of displaying an image by using a display unit disposed on a head support and a mirror 430.

Figure 12B:
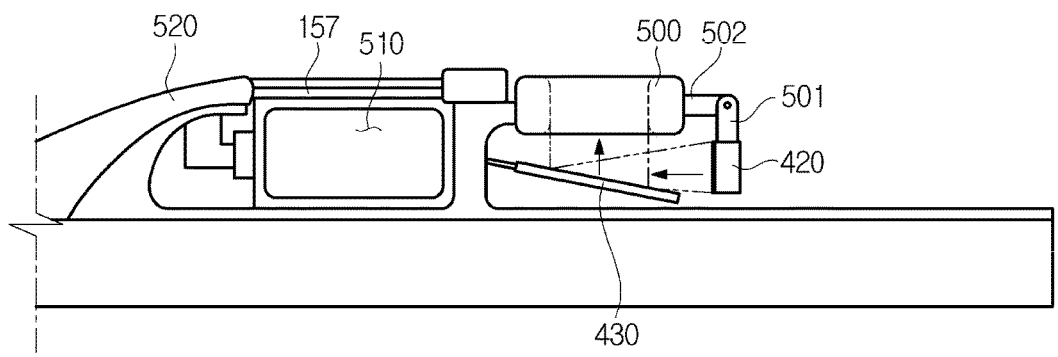
FIG. 12B a cross-sectional view of the magnetic resonance imaging apparatus, according to the exemplary embodiment illustrated in FIG. 11, illustrating an example of displaying an image by using a display unit disposed on a head support and a mirror.

As illustrated in FIGS. 12A and 12B, in the magnetic resonance imaging apparatus 100, the abdomen support 520, the chest support 510, and the head support 500 are sequentially disposed, and the table 180 is disposed below the bottom surface of the support. A GUI image is displayed between the head support 500 and the table 180.

In particular, the mirror 430 is disposed not to be parallel to the table 180, but instead to be inclined toward the display 420 such that an image displayed on the display 420 is visible via the supporting hole 505.

In addition, the display 420 may be disposed to be spaced apart from the head support 500 by a predetermined distance.

In particular, as illustrated in FIG. 12A, the display 420 may enable the displayed image to be seen through the supporting hole 505 via regular reflection by the mirror 430 in a state of being disposed on the table 180. As illustrated in FIG. 12B, the display 420 may enable the displayed image to be seen through the supporting hole 505 in a state of being connected to the connection arm which is disposed on the head support 500.

The screen 440 may also be detachable for image capturing, if required. In particular, referring to FIG. 12B, the connection arm may include a detachable arm 502 and a fixing arm 501. In this regard, the detachable arm 502 which functions as a connector may be detachably connected to the head support 500, and the fixing arm 501 may fix and support the display 420 in a state of being connected to the detachable arm 502.

Hereinafter, a method for displaying a GUI image by using glasses according to an exemplary embodiment will be described with reference to FIGS. 13A and 13B.

Figure 13A:
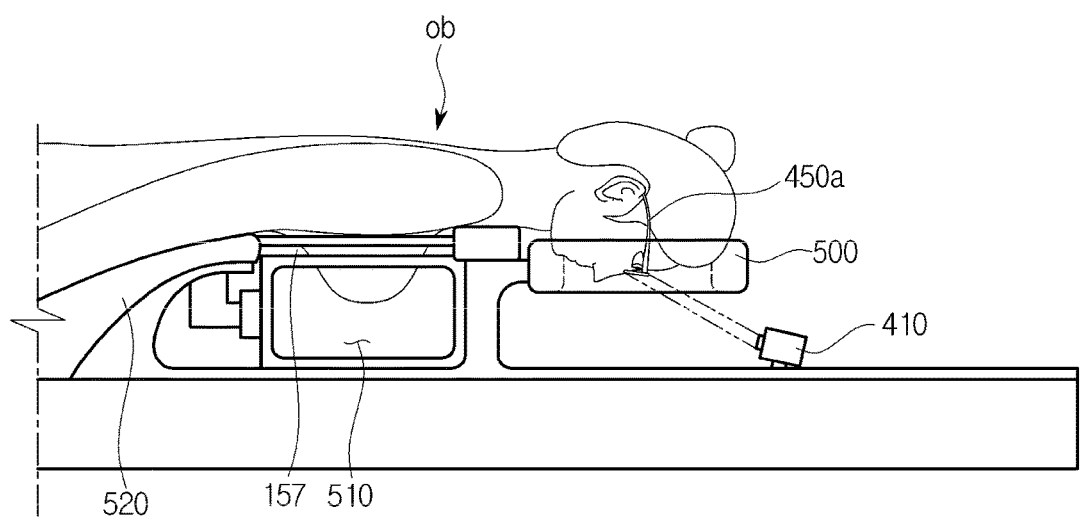
FIG. 13A is a diagram illustrating an example of displaying an image by using a projector and projection glasses, according to an exemplary embodiment.

FIG. 13A illustrates an example of displaying an image by using a projector and projection glasses.

As illustrated in FIG. 13A, a face of an object ob wearing a pair of projection glasses 450a is supported by the supporting hole 505, so that the projection glasses 450a are located at a lower portion of the head support 500.

A screen is disposed at a frame of the projection glasses 450a, and an image to be displayed via diffused reflection of light beams projected by the projector 410 is formed on the screen of the projection glasses 450a. In addition, the screen may be disposed at respective positions adjacent to both eyes of the object ob, or at one position adjacent to one eye of the object ob.

In addition, the projector 410 disposed on the table 180 may project light beams to the screen of the projection glasses 450a disposed in the supporting hole 505. The projector 410 may also project a plurality of light beams in accordance with the number of screens disposed at the projection glasses 450a, or a plurality of screens may be used.

In addition, the image to be displayed on the screen by using the light beams projected by the projector 410 may be formed by backward projection.

Figure 13B:
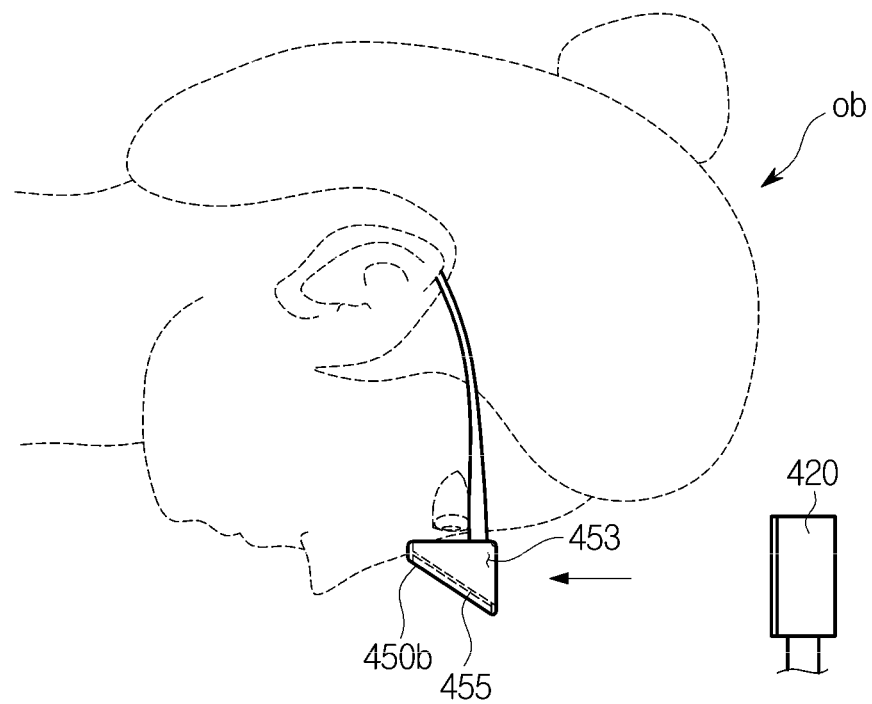
FIG. 13B is a diagram illustrating an example of displaying an image by using a display unit and reflection glasses, according to an exemplary embodiment.

FIG. 13B illustrates an example of displaying an image by using a display unit and reflection glasses.

A mirror 455 is disposed on a frame of a pair of reflection glasses 450b, so that an image displayed on a display 420 may be introduced into the supporting hole 505.

In particular, the display 420 is disposed to be spaced apart from the head support 500 by a predetermined distance, and an image is displayed on the display 420. The image displayed on the display 420 is introduced onto the mirror 455 via an inlet 453 of the mirror 455, and the introduced image is redirected to eyes of the object ob via regular reflection.

In addition, the display 420 may be disposed to be spaced apart from the head support 500 by a predetermined distance, and one display or a plurality of displays may be used in accordance with an angle of the mirror 455 disposed at the reflection glasses 450b.

Hereinafter, a magnetic resonance imaging apparatus which includes a darkroom housing according to an exemplary embodiment will be described with reference to FIGS. 14A and 14B.

Figure 14A:
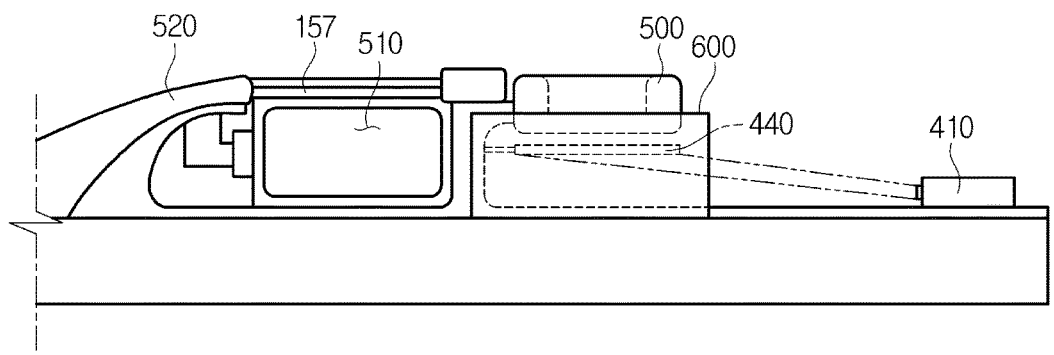
FIG. 14A is a cross-sectional view of a magnetic resonance imaging apparatus including a darkroom housing, according to an exemplary embodiment.
Figure 14B:
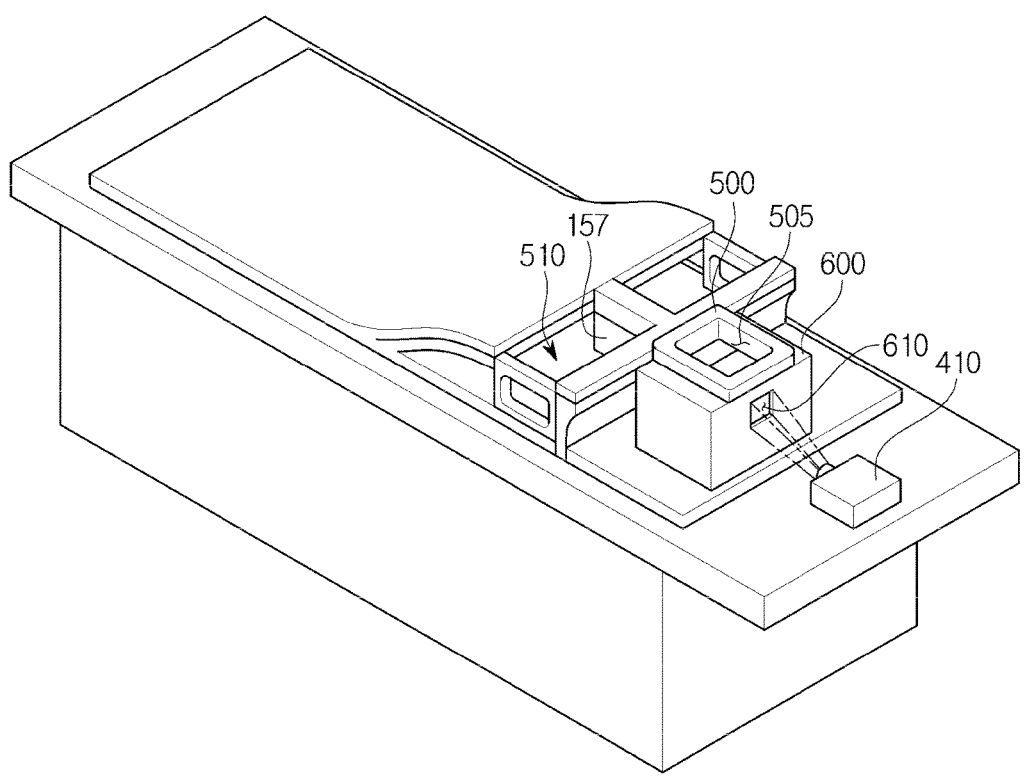
FIG. 14B is a perspective view of a magnetic resonance imaging apparatus including a darkroom housing, according to an exemplary embodiment.

FIG. 14A is a cross-sectional view of a magnetic resonance imaging apparatus which includes a darkroom housing. FIG. 14B illustrates an external appearance of the magnetic resonance imaging apparatus which includes the darkroom housing.

Visibility of a display unit 400 of the magnetic resonance imaging apparatus 100 may be determined by an ambient environment.

In particular, as a brightness of the ambient environment increases, a corresponding visibility of an image displayed on the display unit 400 may decrease. This is because, in the image transmitted by the projector 410 or display 420, an intensity of light transmitted by a light source may be reduced in accordance with the brightness of the ambient environment. Thus, as illustrated in FIGS. 14A and 14B, a brightness of a visible region of the object ob may be controlled independently from the ambient lighting of the magnetic resonance imaging apparatus 100 by using a darkroom housing 600.

In this aspect, light beams projected by the projector 410 are introduced into the darkroom housing 600 via the inlet 610 of the darkroom housing 600 and transmitted to the screen 440, so that the image is displayed on the screen 440.

Hereinafter, a magnetic resonance imaging apparatus which is usable for performing a biopsy according to an exemplary embodiment will be described with reference to FIG. 15.

Figure 15:
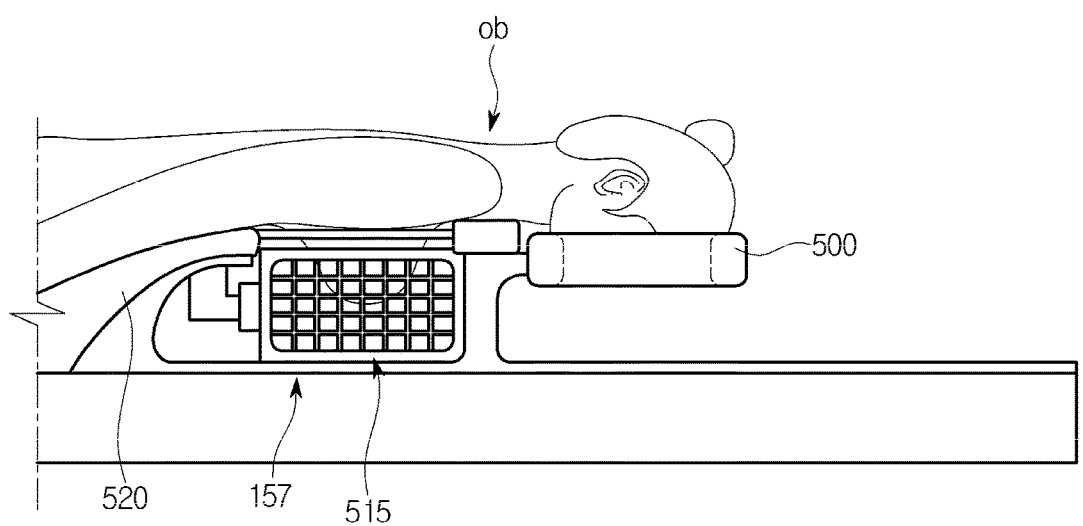
FIG. 15 is a diagram illustrating a magnetic resonance imaging apparatus which is configured for use in relation to performing a biopsy, according to an exemplary embodiment.

FIG. 15 illustrates a magnetic resonance imaging apparatus which is configured to be used for performing a biopsy.

A biopsy is performed by removing a target soft tissue based on an acquisition of an image of the soft tissue via magnetic resonance imaging, and then confirming whether the soft tissue has been successfully removed by acquiring a magnetic resonance image thereof.

For example, in a soft tissue biopsy of a breast of an object ob, a magnetic resonance image of the breast is acquired, and then the table 180 is moved out of the cavity. Then, an insertion member is inserted into the breast tissue based on the acquired image. In this case, grids 515 may be disposed at both sides of the chest support 510 in order to guide the insertion member to a desired position based on the acquired image. Then, after the table 180 is moved into the cavity and a magnetic resonance image thereof is acquired, the table 180 is moved out of the cavity again to confirm whether the insertion member is located near the target tissue, and the target tissue is removed. Then, a determination is made as to whether the specific tissue has been successfully removed by moving the table 180 into the cavity and acquiring a magnetic resonance image thereof.

Hereinafter, a magnetic resonance imaging apparatus which includes an input unit according to an exemplary embodiment will be described with reference to FIG. 16.

Figure 16:
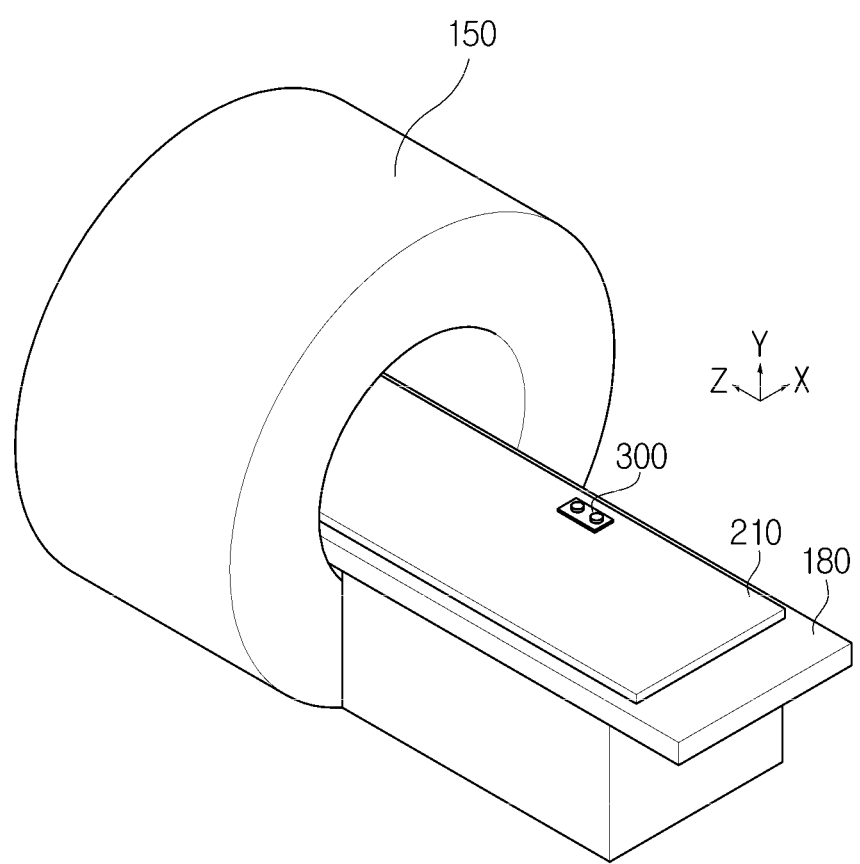
FIG. 16 is a perspective view of a magnetic resonance imaging apparatus which includes an input unit, according to an exemplary embodiment.

FIG. 16 illustrates an external appearance of a magnetic resonance imaging apparatus which includes an input unit.

The object ob may transmit an input signal to a controller via an input unit (also referred to herein as an "input device") 300 such that a GUI image which relates to the current status, remaining time, and the like is selected and controlled during a magnetic resonance imaging process.

The input unit 300 may be a button type input unit disposed at a side of the table 180 as illustrated in FIG. 16, or may be a slide type input unit disposed at a side of the table 180. Alternatively, the input unit 300 may be a remote control type input unit which is usable by the object ob in the cavity. Any other of various types of input units may also be used as the input unit 300.

As is apparent from the above description, the magnetic resonance imaging apparatus according to one or more exemplary embodiments may display an image between a head support and a table while an object is lying prone facing the table.

Although a few exemplary embodiments have been shown and described, it will be appreciated by those of skill in the art that changes may be made in these exemplary embodiments without departing from the principles and spirit of the present disclosure, the scope of which is defined in the claims and their equivalents.

What is claimed is:

1. A magnetic resonance imaging apparatus comprising:
a table disposed in a cavity which is formed in a bore;
a head support having a support hole where a face of an object disposed on the table is positioned;
an abdomen support having a slope to support an abdomen of the object;
a display configured to display a graphical user interface (GUI) image, the display being disposed between the table and the head support, the display comprising a projector configured to project the GUI image and a screen on which the GUI image projected by the projector is displayed; and
a guide configured to facilitate a vertical movement of the projector;
wherein an upper surface of the table is visible to the object through the support hole,
wherein the guide has a curved shape to form the GUI image projected by the projector while vertically moving on the screen, and
wherein the screen is configured to vertically move between the head support and the upper surface of the table, in accordance with a changing position of the projector.

2. The magnetic resonance imaging apparatus according to claim 1, wherein the projector is further configured to project the GUI image onto a back surface of the screen.

3. The magnetic resonance imaging apparatus according to claim 1, wherein the projector is further configured to project the GUI image onto a front surface of the screen.

4. The magnetic resonance imaging apparatus according to claim 1, wherein the display further comprises a mirror configured to reflect the GUI image projected by the projector toward the screen, and
the projector is further configured to project the GUI image onto the mirror such that the GUI image is reflected by the mirror onto the screen.

5. The magnetic resonance imaging apparatus according to claim 1, wherein the projector is disposed on the table or off of the table.

6. The magnetic resonance imaging apparatus according to claim 1, wherein the projector is detachably disposed on the head support.

7. The magnetic resonance imaging apparatus according to claim 1, wherein the display comprises a display device on which the GUI image is displayed and a mirror configured to reflect the displayed GUI image toward eyes of the object.

8. The magnetic resonance imaging apparatus according to claim 1, wherein the display comprises a pair of glasses on which an image projected by the projector is formed.

9. The magnetic resonance imaging apparatus according to claim 1, wherein the display comprises a display device on which the GUI image is displayed and a pair of glasses configured to reflect the GUI image displayed on the display device toward eyes of the object.

10. The magnetic resonance imaging apparatus according to claim 1, further comprising a darkroom housing configured to control a brightness between the table and the head support.

11. The magnetic resonance imaging apparatus according to claim 1, further comprising an input device configured to facilitate a control of the displayed GUI image.

12. A method for displaying an image generated by a magnetic resonance imaging apparatus which includes a table disposed in a cavity which is formed in a bore, a head support having a support hole where a face of an object disposed on the table is positioned, an abdomen support having a slope to support an abdomen of the object, a projector configured to project the image, and a screen on which the projected image is displayable, wherein an upper surface of the table is visible to the object through the support hole, the method comprising:
  arranging the screen with respect to the table and the head support;
  arranging the projector with respect to the table and the head support; and
  projecting, by the projector, the image onto a surface of the screen,
  wherein the arranging the projector comprises connecting the projector to a guide member which has a curved shape and which is configured to facilitate a vertical movement of the projector with respect to the table,
  wherein the projecting comprises projecting light beams onto the surface of the screen, and
  wherein the arranging the screen comprises arranging the screen between the head support and the upper surface of the table, in accordance with a change position of the projector.

13. The method of claim 12, wherein the arranging the screen comprises arranging the screen to be parallel to the table at a predetermined height with respect to the upper surface of the table,
  the arranging the projector comprises arranging the projector directly on the table, and
  the projecting comprises projecting light beams onto a back surface of the screen.

14. The method of claim 12, wherein the arranging the screen comprises arranging the screen to be parallel to the table at a predetermined height with respect to the upper surface of the table,
  the arranging the projector comprises connecting the projector to a connection arm which is disposed on the head support, and
  the projecting comprises projecting light beams onto a back surface of the screen.

15. The method of claim 12, wherein the arranging the screen comprises arranging the screen to be lying flat on the upper surface of the table,
  the arranging the projector comprises arranging the projector directly on the table, and
  the projecting comprises projecting light beams onto a mirror such that the mirror redirects the projected light beams onto a front surface of the screen.

16. The method of claim 12, wherein the arranging the screen comprises arranging the screen to be lying flat on the upper surface of the table,
  the arranging the projector comprises connecting the projector to a connection arm which is disposed on the head support, and
  the projecting comprises projecting light beams onto a mirror such that the mirror redirects the projected light beams onto a front surface of the screen.

17. The method of claim 12, wherein the arranging the screen comprises arranging the screen to be nonparallel to the upper surface of the table,
  the arranging the projector comprises arranging the projector directly on the table, and
  the projecting comprises projecting light beams onto a front surface of the screen.

18. The method of claim 12, wherein the arranging the screen comprises arranging the screen such that the screen is nonparallel to the upper surface of the table, the arranging the projector comprises connecting the projector to a connection arm which is disposed on the head support, and the projecting comprises projecting light beams onto a front surface of the screen.

19. The method of claim 12, wherein the arranging the screen comprises arranging the screen to be lying flat on the upper surface of the table,
  the arranging the projector comprises arranging the projector at a predetermined height via a connection arm which is directly connected to the table, and
  the projecting comprises projecting light beams onto a front surface of the screen.

20. The method of claim 12, wherein the arranging the screen comprises arranging the screen to be lying flat on the upper surface of the table, the arranging the projector comprises arranging the projector at a predetermined height via a connection arm which is disposed on the head support, and the projecting comprises projecting light beams onto a front surface of the screen.

21. The method of claim 12, wherein the arranging the screen comprises arranging the screen to be parallel to the upper surface of the table at a predetermined height with respect to the upper surface of the table.

22. The method of claim 12, wherein the arranging the screen comprises arranging the screen on a pair of glasses to be worn by the object,
  the arranging the projector comprises arranging the projector directly on the table, and
  the projecting comprises projecting light beams onto the surface of the screen.

23. The method of claim 12, wherein the magnetic resonance imaging apparatus further includes a darkroom housing within which the screen is housed, and the method further comprises controlling a brightness of an ambient environment with the darkroom housing so as to enhance a visibility of the image.

* * * * *